United States Patent [19]
Cameron

[11] Patent Number: 5,059,170
[45] Date of Patent: Oct. 22, 1991

[54] CONNECTION ADAPTER FOR CATHETERS

[75] Inventor: Michael S. Cameron, South Glens Falls, N.Y.

[73] Assignee: Mallinckrodt Medical, Inc., St. Louis, Mo.

[21] Appl. No.: 474,971

[22] Filed: Feb. 2, 1990

[51] Int. Cl.$^5$ .............................................. A61M 3/00
[52] U.S. Cl. ................................... 604/43; 604/280; 604/283; 604/905
[58] Field of Search ............ 604/280, 283, 284, 43–45, 604/905, 256

[56] References Cited

U.S. PATENT DOCUMENTS

| | | | |
|---|---|---|---|
| 3,599,641 | 8/1971 | Sheridan | 604/256 |
| 4,403,983 | 9/1983 | Edelman | 604/43 |
| 4,701,159 | 10/1987 | Brown et al. | 604/43 |
| 4,776,841 | 10/1988 | Catalano | 604/43 |
| 4,895,561 | 1/1990 | Mahurkar | 604/283 |
| 4,969,879 | 11/1990 | Lichte | 604/283 |

Primary Examiner—Stephen C. Pellegrino
Assistant Examiner—Michael Rata
Attorney, Agent, or Firm—David A. Hey

[57] ABSTRACT

The present invention relates to an adapter for connecting a multiple lumen catheter to a corresponding number of single lumen supply tubes, which allows access for further devices such as a bronco-scope or a suction catheter. The adapter comprises; a one-piece molded multiple lumen body, each lumen of the adapter body corresponding directly to a desired connection between the multiple lumen catheter and a corresponding number of single lumen supply tubes.

16 Claims, 3 Drawing Sheets

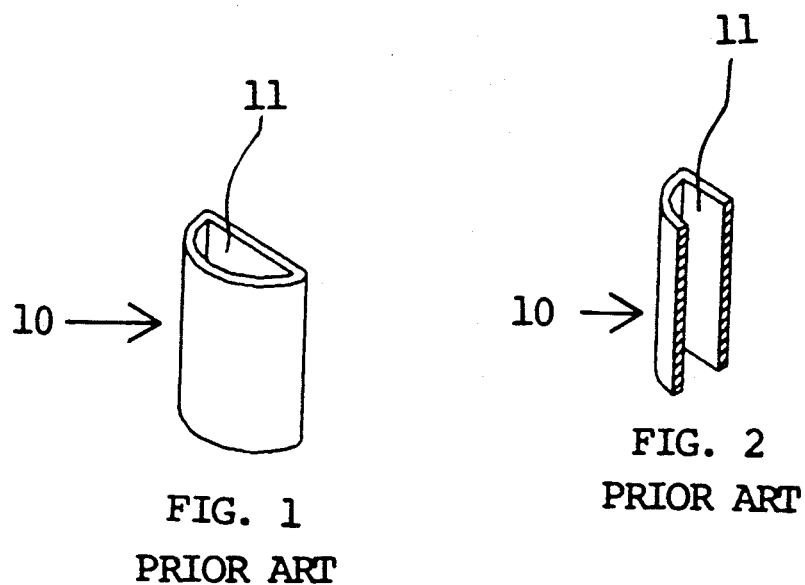
FIG. 1 PRIOR ART
FIG. 2 PRIOR ART
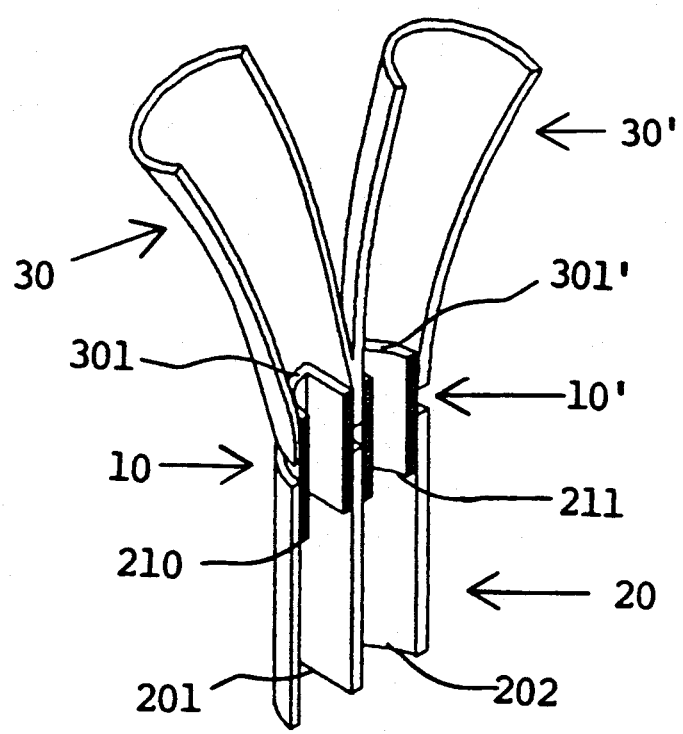
FIG. 3 PRIOR ART

CONNECTION ADAPTER FOR CATHETERS

BACKGROUND OF THE INVENTION

The present invention relates to improvements in adapters for connecting catheters to supply tubes. In particular, the present invention relates to an adapter for connecting a multiple lumen catheter to a corresponding number of single lumen supply tubes, which allows access for further devices such as a bronco-scope or a suction catheter.

Known adapters comprise tubular members which are inserted into the interior diameter of both the catheter lumen and the corresponding supply tube lumen. In the prior art, a separate adapter is required for each catheter lumen to supply tube lumen connection.

The prior art adapters have several disadvantages and drawbacks. In particular, as noted above, in the prior art, a separate adapter is required for each catheter lumen to supply tube lumen connection (i.e. two adapters are required when using a double lumen catheter and two single lumen supply tubes). Because separate adapters must be inserted separately, a relatively high degree of force and level of manual dexterity are required. This can lead to the production of particulates or lumen restriction by skiving of the inside of the catheter lumens during assembly. Further, cumulative trauma disorders may be caused during the difficult insertion process.

The prior art adapters are made by a extrusion process in which the material making up the adapter is drawn and shaped into the desired configuration. This type of plastic deformation process creates a product having disadvantageous strength and rigidity. Therefore, partial collapsing of the adapters by the pressure of the catheter lumen may occur because of stresses at the distal edge of the adapter.

Moreover, because the adapter fits into the interior of both the catheter lumens and supply tube lumens, when fully assembled, the adapter ends present an edge which may act as a barrier or snag to the incoming tip of a secondary device, such as a bronco-scope or suction catheter.

THE OBJECTS OF THE INVENTION

It is an object of the present invention to overcome the disadvantages associated with prior art adapters and to provide an improved adapter for connection of multiple lumen catheters to a corresponding number of single lumen supply tubes.

Further, it is an object of the present invention to provide an adapter which comprises a single molded piece for connecting a multiple lumen catheter to a corresponding number of single lumen supply tubes.

SUMMARY OF THE INVENTION

The above objects and more are achieved by providing an adapter according to the present invention which comprises; a molded one-piece multiple lumen body, each lumen of the adapter body corresponding directly to a desired connection between a multiple lumen catheter and a corresponding number of single lumen supply tubes.

The adapter body includes a proximal end portion having a plurality of generally circular cross-section lumens extending for a length sufficient to enable adequate insertion of a single lumen supply tube in each of the plurality of adapter lumens.

The adapter body further includes a distal end portion having a plurality of lumens extending for a length sufficient to enable adequate insertion of each lumen into a lumen contained in a multiple lumen catheter. Each of the lumen openings at the distal end portion of the adapter have a cross-sectional area corresponding to equal portions of a circle, i.e. each circle portion being equal to three hundred and sixty degrees divided by the total number of lumens.

The adapter body also includes a middle portion having a plurality of lumens having changing cross-sections, each lumen extending from a generally circular cross-section adjacent to the proximal end portion of the adapter to a generally circular portion cross-section adjacent to the distal end portion of the adapter. The middle portion of the adapter body may also include a semi-conical direction orienting construction along at least part of its length.

The proximal end portion, distal end portion and middle body portion make up a continuous one-piece adapter having a plurality of continuous lumens running through the length of the adapter. The lumens share a common wall through the proximal end and middle body portions. The lumens are separated from each other throughout the distal end portion so as to constitute separate insertion ends for attachment to the multiple lumen catheter. Further, the lumens are of a size adapted to allow passage of surgical devices such as a bronco-scope and a suction catheter or the like, into the multiple lumen catheter.

One advantage of the adapter according to the present invention is that a relatively small degree of force and level of manual dexterity is required in order to insert the adapter between a multiple lumen catheter and a corresponding number of single lumen supply tubes.

Moreover, the adapter according to the present invention avoids skiving of the inside of the catheter and supply tube lumens during insertion of the adapter therein.

Also, the adapter according to the present invention reduces the occurrence of cumulative trauma disorders caused by connection of multiple lumen catheters to a corresponding number of single lumen supply tubes.

Furthermore, the adapter according to the present invention is dimensionally stable and reduces stress at the distal edges of the adapter, to thereby avoid partial collapse of the adapter upon insertion into the catheter and supply tube lumens.

Another advantage of the adapter according to the present invention is that when the adapter is used to connect a multiple lumen catheter to a corresponding number of single lumen supply tubes, there are no exposed edges or corners which may create a barrier or snag to an incoming tip of a secondary device, e.g. a bronco-scope or suction catheter.

The adapter according to the present invention may further include a funnel-shaped transition between the single lumen supply tubes and the multiple lumen catheter which assists in guiding the tip of a secondary device towards the center, and largest area, of the lumen.

The adapter according to the present invention will be described in greater detail below with reference to the drawing figures.

BRIEF DESCRIPTION OF THE DRAWINGS

FIG. 1 is a plan view of a prior art adapter for connecting catheters to supply tubes.

FIG. 2 is a cross-sectional view of the prior art adapter shown in FIG. 1.

FIG. 3 is a cross-sectional view of a catheter to supply tube connection using two prior art adapters as shown in FIG. 1.

DETAILED DESCRIPTION OF THE INVENTION

Figure 4:
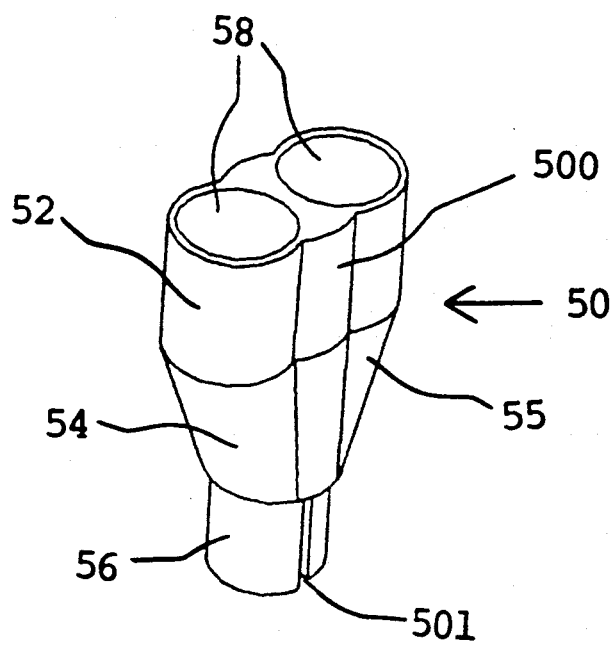
FIG. 4 is a plan view of the adapter according to one aspect of the present invention for connecting a multiple lumen catheter to a corresponding number of single lumen supply tubes.

FIG. 1 shows a plan view and FIG. 2 shows a cross-sectional view of an adapter known in the prior art which may be used to connect a catheter to a supply tube. The adapter generally indicated by reference numeral 10, has the form of an elongated cylinder or tube, and includes a lumen 11, having a D-shaped cross-section throughout its length.

FIG. 3 shows a cross-sectional view of a catheter to supply tube connection using two prior art adapters as shown in FIG. 1. A catheter, generally designated by reference numeral 20, has two lumens, 201, 202 which are connected to separate supply lines 30, 30' through two adapters 10, 10'. To achieve this connection, the adapters must be inserted individually into the catheter lumens and to the corresponding supply tube lumens. This requires a relatively high degree of force and level of manually dexterity which can lead to particulate formation and lumen restriction caused by skiving of the insides of the catheter and supply tube lumens. Moreover, cumulative trauma disorders may occur during the difficult insertion process. The adapters 10, 10' are formed by an extrusion process and therefore partial collapse of the adapters by the pressure of the catheter lumen may also occur because of stresses of the distal edges of the adapters, 210, 211. In addition, the adapters 10, 10' are inserted into the lumens of the supply tubes, 30, 30' and therefore form an edge 301, 301'. This edge 301, 301' may act as a barrier or snag to the incoming tip of a secondary device such as a broncoscope or suction catheter (not shown).

The adapter according to the present invention overcomes most or all of the disadvantages associated with the prior art adapters, and is illustrated in FIGS. 4–9.

Figure 5:
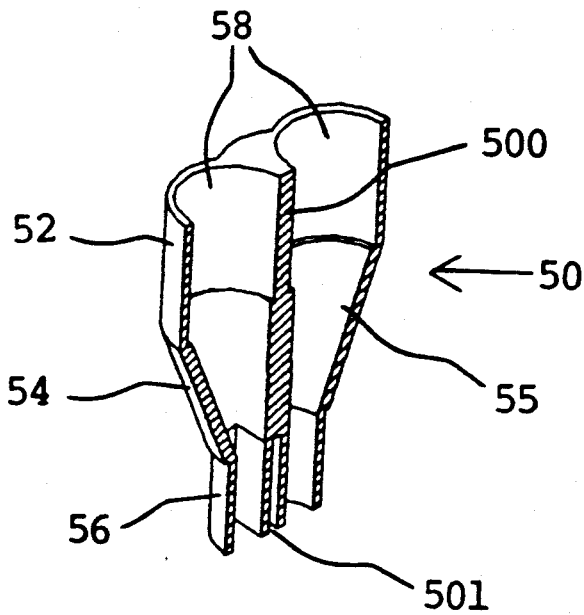
FIG. 5 is a cross-sectional view of the adapters shown in FIG. 4.
Figure 6:
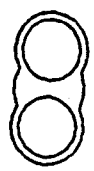
FIGS. 6(a) and (b) are end views of a two lumen adapter according to the present invention showing the configuration of the lumens at the proximal end and distal end, respectively.
Figure 6:

FIG. 4 is a plan view and FIG. 5 is a cross-sectional view of an adapter for connecting a double-lumen catheter to two supply tubes in accordance with the present invention. The adapter, generally designated by reference numeral 50, includes a proximal end portion 52, a middle portion 54, and a distal end portion 56. The adapter 50, has two lumens 58, which extend throughout the length of the adapter. Each lumen 58, has a generally circular cross-section at its opening in the proximal end portion 52, and a cross-section of its openings in the distal end portions 56, corresponding to equal portions of a circle. In the embodiment in FIG. 4, the adapter 50, includes two lumens 58, wherein the cross-section of each of the distal end portions are D-shaped or correspond to a half-circle. The lumens 58, are connected along their respective lengths throughout the proximal end portion 52, and middle portion 54, of the adapter 50, by material 500. The distal end portions 56, of the lumens 58, are separated by a gap 501, in order to form separate lumens for insertion into a catheter. The middle portion 54, of the adapter 50, includes a semi-conical direction-orienting section 55, which acts to direct the tip of a secondary device (not shown) towards the center and largest area of each lumen 58.

FIGS. 6(a) and 6(b) are end views of a two lumen adapter according to the present invention showing the configuration of the lumens of the proximal end and distal end, respectively. When a two lumen adapter is desired, the cross-sectional area of each lumen at the proximal end of the adapter corresponds to a circle. The cross-sectional area of each lumen at the distal end of the adapter corresponds to a half-circle or generally to a D-shape.

Figure 7:
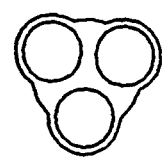
FIGS. 7(a) and (b) are end views of a three lumen adapter according to the present invention showing the configuration of the lumens at the proximal end and distal end, respectively.
Figure 7B:
Figure 8:
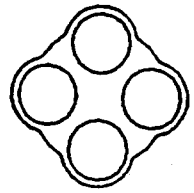
FIGS. 8(a) and (b) are end views of a four lumen adapter according to the present invention showing the configuration of the lumens at the proximal end and distal end respectively.
Figure 8:

FIG. 7(a) and 7(b) are end views of a three lumen adapter according to the present invention showing the configuration of the lumens at the proximal end and distal end, respectively. When a three-lumen adapter is desired, the cross-sectional area of each lumen at the proximal end of the adapter corresponds to a circle. The cross-sectional area of each lumen at the distal end of the adapter corresponds to a third of a circle or to 120 degrees of a circle.

FIGS. 8(a) and 8(b) are end views of a four lumen adapter according to the present invention showing the configuration of the lumens at the proximal end and distal end, respectively. When a four lumen adapter is desired, the cross-sectional area of each lumen at the proximal end of the adapter corresponds to a circle. The cross-sectional area of each lumen at the distal end of the adapter corresponds to a fourth of a circle or to 90 degrees of a circle.

Figure 9:
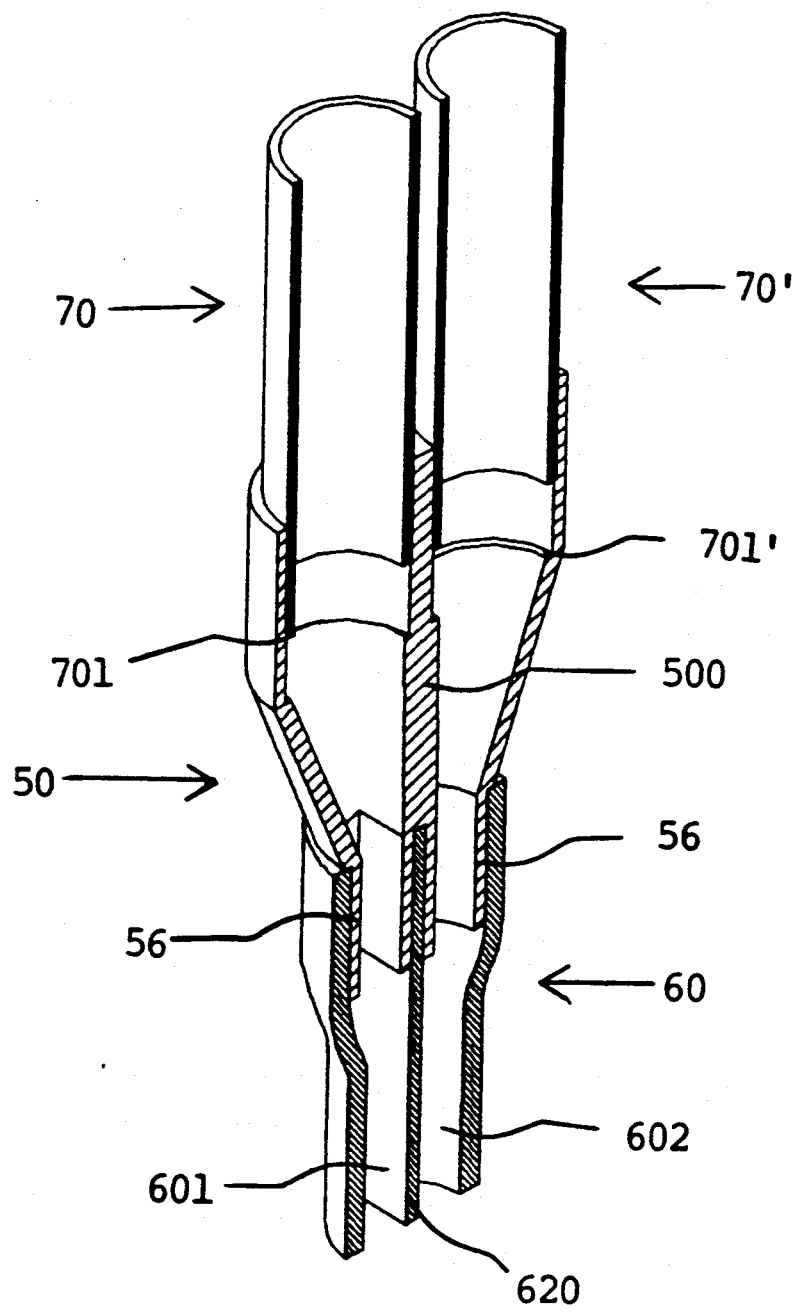
FIG. 9 is a cross-sectional view of a catheter to supply tube connection using an adapter according to the present invention as shown in FIG. 4.

FIG. 9 shows a cross-sectional view of a catheter to supply tube connection using an adapter according to the present invention shown in FIG. 4. A catheter, generally designated by reference numeral 60, has two lumens 601, 602, which are connected to separate supply tubes 70, 70', by a single-piece molded adapter 50, according to the present invention. To achieve this connection, the two distal ends 56, of the adapter 50, are inserted simultaneously into the lumens 601, 602 of the catheter 60. Such insertion requires a relatively small degree of force and manual dexterity and thus reduces skiving and the formation of particulate lumen restriction. Because the adapter 50, is molded, the distal end portions 56, have sufficient rigidity to withstand stresses upon insertion into the catheter 60, and therefore, collapse of the adapter 50, caused by pressure of the catheter lumens 601, 602 may be avoided. It is noted that the gap 501, (FIGS. 4 and 5) between the distal end portions 56, is proportioned so as to correspond to the space occupied by the material 620, connecting the lumens 601, 602, of the catheter 60. The connection is completed by inserting the supply tubes 70, 70,' into the lumens at the proximal end of the adapter 50. Because the supply tubes 70, 70', are inserted into the adapter 50, the edges 701, 701', do not create an edge and, therefore, pose no barrier or snag to the tip of an incoming secondary device (not shown). This in turn allows smoother and easier insertion of such devices; reduces danger to the patient; and reduces the possibility of damaging or rendering inoperable the secondary device.

The adapter according to the present invention is formed in one piece by a suitable molding process. Any rigid clear plastic having suitable rigidity and pliability upon molding may be used. In particular the plastic materials used should be soft to semi-rigid and be able to withstand standard ageing, collapse and pull tests. It is preferable that the adapters according to the present invention be made of clear acryl butyl styrene (ABS), acrylic, or rigid polyvinyl chloride (PVC). Most preferably, the adapter according to the present invention should be made of clear ABS by an injection molding process. In particular, the adapter according to the present invention may be formed by a standard injection molding process, wherein a multi cavity injection mold body is used. The mold body may contain interchangeable die cavities and die pins to facillitate molding of different adapter sizes. When the desired cavities and pins have been inserted into the mold body, the mold body is fixed into an injection molding machine and chosen thermoplastic material is injected into the mold. The molded adapters are then allowed to cool and are ejected from the mold cavities. The adapters are then ready to be assembled onto an appropriate device.

What is claimed is:

1. An adapter for connecting a multiple lumen catheter to a corresponding number of single lumen supply tubes, the adapter comprising:
   a one piece molded body having a distal end and a proximal end; and having a plurality of lumens extending throughout the length of said body, the number of lumens corresponding to the number of lumens in said multiple lumen catheter, said body including;
     a first body portion wherein each of said plurality of lumens has a generally circular cross-section and extend for a length sufficient to allow adequate insertion of said supply tubes therein;
     a second body portion wherein each of said plurality of lumens has a cross-section generally corresponding to equal sections of a circle and extend for a length sufficient to allow adequate insertion into individual lumens of said multiple lumen catheter; and
     a third body portion connecting said first and second body portions wherein each of said plurality of lumens has a cross-section at one end which corresponds with the cross-sections of said plurality of lumens in said first body portion and a cross-section at the other end which corresponds with the cross-sections of said plurality of lumens in said second body portion;
   wherein said plurality of lumens are connected along the entire lengths of their respective first and third body portions and are spaced apart along the entire length of their respective second body portions so as to constitute insertion ends for insertion into individual lumens of said multiple lumen catheter, and
   wherein said third body portion of said adapter further includes a semi-conical direction orienting section associated with each of said plurality of lumens and extending along at least a part of the length of said third body portion.

2. An adapter according to claim 4, wherein each of the plurality of lumens of said adapter are of a size adapted to allow passage of surgical devices therethrough.

3. An adapter according to claim 1, wherein said semi-conical direction orienting section is adapted to direct a tip of a surgical device toward the center and largest area of an associated lumen.

4. An adapter according to claim 1, wherein said adapter includes two lumens, wherein each of said two lumens has a cross-section in said second body portion of said adapter which is D-shaped or corresponds to a half-circle.

5. An adapter according to claim 1, wherein said adapter includes three lumens, wherein each of said three lumens has a cross-section in said second body portion of said adapter which corresponds to 120 degrees of a circle.

6. An adapter according to claim 1, wherein said adapter includes four lumens, wherein each of said four lumens has a cross-section in said second body portion of said adapter which corresponds to 90 degrees of a circle.

7. An adapter according to claim 1, wherein said adapter is formed of a rigid clear plastic.

8. An adapter according to claim 7, wherein said rigid clear plastic is selected from the group consisting of clear acryl butyl styrene, acrylic and rigid polyvinyl chloride.

9. A catheter system including a multiple lumen catheter, a corresponding number of single lumen supply tubes and an adapter for connecting said multiple lumen catheter to said supply tubes; the adapter comprising:
   a molded one piece body having a distal end and a proximal end; and having a plurality of lumens extending throughout the length of said body, the number of lumens corresponding to the number of lumens in said multiple lumen catheter, said body including;
     a first body portion wherein each of said plurality of lumens has a generally circular cross-section and extend for a length sufficient to allow adequate insertion of said supply tubes therein;
     a second body portion wherein each of said plurality of lumens has a cross-section generally corresponding to equal sections of a circle and extend for a length sufficient to allow adequate insertion into individual lumens of said multiple lumen catheter; and
     a third body portion connecting said first and second body portions wherein each of said plurality of lumens has a cross-section at one end which corresponds with the cross-sections of said plurality of lumens in said first body portion and a cross-section at the other end which corresponds with the cross-sections of said plurality of lumens in said second body portion;
   wherein said plurality of lumens are connected along the entire lengths of their respective first and third body portions and are spaced apart along the entire length of their respective second body portions so as to constitute insertion ends for insertion into individual lumens of said multiple lumen catheter, and wherein said third body portion of said adapter further includes a semi-conical direction orienting section associated with each of said plurality of lumens and extending along at least a part of the length of said third body portion.

10. An adapter according to claim 9, wherein each of the plurality of lumens of said adapter are of a size adapted to allow passage of surgical devices therethrough.

11. An adapter according to claim 9, wherein said semi-conical direction orienting is adapted to direct a tip of a surgical device toward the center and largest area of an associated lumen.

12. An adapter according to claim 9, wherein said adapter includes two lumens, wherein each of said two lumens has a cross-section in said second body portion of said adapter which is D-shaped or corresponds to a half-circle.

13. An adapter according to claim 9, wherein said adapter includes three lumens, wherein each of said three lumens has a cross-section in said second body portion of said adapter which corresponds to 120 degrees of a circle.

14. An adapter according to claim 9, wherein said adapter includes four lumens, wherein each of said four lumens has a cross-section in said second body portion of said adapter which corresponds to 90 degrees of a circle.

15. An adapter according to claim 9, wherein said adapter is formed of a rigid clear plastic.

16. An adapter according to claim 15, wherein said rigid clear plastic is selected from the group consisting of clear acryl butyl styrene, acrylic and rigid polyvinyl chloride.

* * * * *